United States Patent [19]

Walsh

[11] Patent Number: 5,248,200

[45] Date of Patent: Sep. 28, 1993

[54] PORTABLE ASPHALT STRESS AND STRAIN MEASURING DEVICE

[75] Inventor: Michael R. Walsh, Weathersfield, Vt.

[73] Assignee: The United States of America as represented by the Secretary of the Army, Washington, D.C.

[21] Appl. No.: 961,797

[22] Filed: Oct. 16, 1992

[51] Int. Cl.⁵ ............................................. G01N 25/00
[52] U.S. Cl. ........................................ 374/45; 374/56; 73/787
[58] Field of Search ................... 374/45, 43, 55, 56; 73/787, 789

[56] References Cited

U.S. PATENT DOCUMENTS

| | | | |
|---|---|---|---|
| 3,554,019 | 1/1971 | Van Den Hove et al. | 73/789 |
| 3,733,049 | 5/1973 | Van Den Hove et al. | 73/789 |
| 4,056,973 | 11/1977 | Prevorsek et al. | 73/789 |
| 4,266,424 | 5/1981 | Muenstedt | 73/789 |
| 4,700,577 | 10/1987 | Tripp | 73/789 |
| 4,798,477 | 1/1989 | Mountain | 374/45 |
| 4,923,307 | 5/1990 | Gilmore et al. | 374/56 |
| 5,009,512 | 4/1991 | Lessi et al. | 374/56 |

FOREIGN PATENT DOCUMENTS

| | | | |
|---|---|---|---|
| 0050737 | 3/1988 | Japan | 73/789 |
| 0053440 | 3/1988 | Japan | 73/789 |
| 0188111 | 10/1966 | U.S.S.R. | 374/45 |
| 1213197 | 3/1986 | U.S.S.R. | 374/45 |
| 2068123 | 8/1981 | United Kingdom | 374/56 |

Primary Examiner—William A. Cuchlinski, Jr.
Assistant Examiner—Diego F. F. Gutierrez

[57] ABSTRACT

A thermally stable fixture for testing asphalt samples is characterized by measurements of both thermal stresses and strains in the sample. The device uses air as the sample cooling or heating fluid for inducing thermal stresses and strains therein. Strains are detected by a linear variable differential transformer mounted on the sample suspended within the fixture. Stresses are detected by a load cell connected with a mounting plate for the sample. Temperatures are detected by temperature sensors attached to the sample and to the fixture for measuring sample and ambient air temperatures, respectively.

3 Claims, 2 Drawing Sheets

PORTABLE ASPHALT STRESS AND STRAIN MEASURING DEVICE

BACKGROUND OF THE INVENTION

During the construction of roads, runways and the like, it is important that the paving asphalt or concrete have the proper composition in accordance with the surrounding environment in order to reduce long-term maintenance costs. The present invention relates to a portable device for on-site evaluation of asphalt samples. Thermal stress and strain data generated by the device is used to tailor the asphalt composition to the specific environment and application.

BRIEF DESCRIPTION OF THE PRIOR ART

Devices for measuring thermal stresses in asphalt are known in the art. Typically, the prior devices could analyze only small asphalt samples up to one square inch. A C-shaped frame is used to hold the sample and a volatile liquid is poured over the sample to induce thermal stresses therein. Because of the requirement for liquid as a cooling fluid and the large size of the prior devices, they are not suitable for on-site analysis. Moreover, two separate temperature control systems are needed to stabilize the apparatus and cool the specimens. Finally, the prior devices are incapable of measuring strains induced in the samples.

The present invention was developed in order to overcome these and other drawbacks of the prior devices by providing a portable device for measuring both thermal stresses and strains in an asphalt pavement sample.

SUMMARY OF THE INVENTION

Accordingly, it is a primary object of the present invention to provide a device for measuring thermal stresses and strains in asphalt samples including a fixture, a pair of mounting plates for suspending the sample within the fixture, and apparatus for directing a flow of variable temperature air onto the sample to induce thermal stresses and strains therein. At least one linear variable differential transformer is mounted on the sample to produce a displacement output signal in response to thermal strain in the sample. A load cell is connected with one of the mounting plates and produces a force output signal in response to thermal stress in the sample.

The fixture includes a cage comprising a plurality of spaced parallel rods having a low coefficient of thermal expansion parallel rods fixed at one end of the housing and a floating end plate connected with the free ends of the rods. One of the mounting plates is connected with the fixed end of the cage and the other mounting plate is connected through the load cell with the cage. The load cell detects axial force generated by the sample on the frame in response to the thermal stress in the sample. Temperature sensors monitor sample and ambient air temperatures.

BRIEF DESCRIPTION OF THE FIGURE

Other objects and advantages of the invention will become apparent from a study of the following specification when viewed in the light of the accompanying drawing, in which.

DETAILED DESCRIPTION

Figure 1:
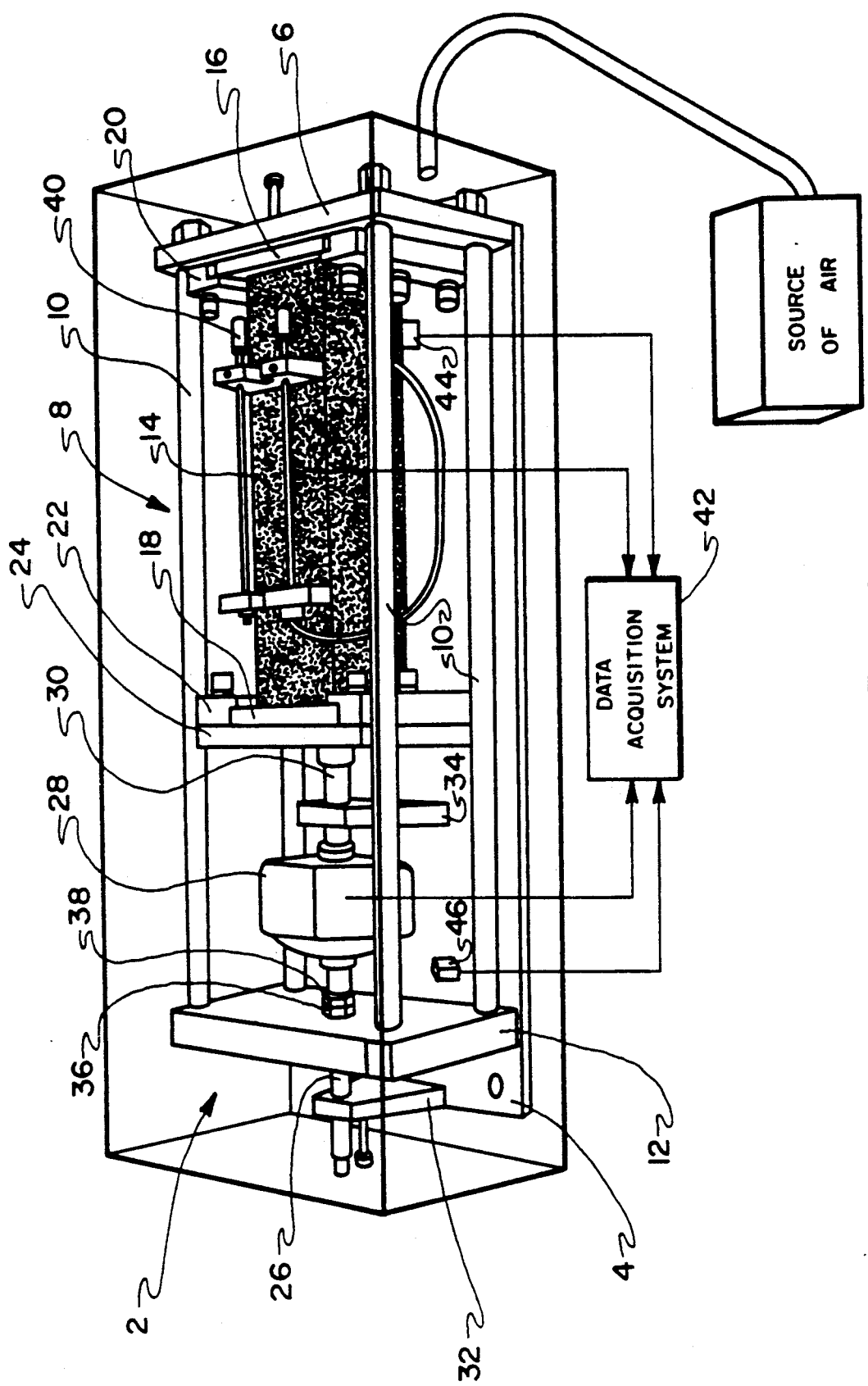
FIG. 1 is a top perspective view of the asphalt sample thermal stress and strain measuring device according to the invention.
Figure 2:
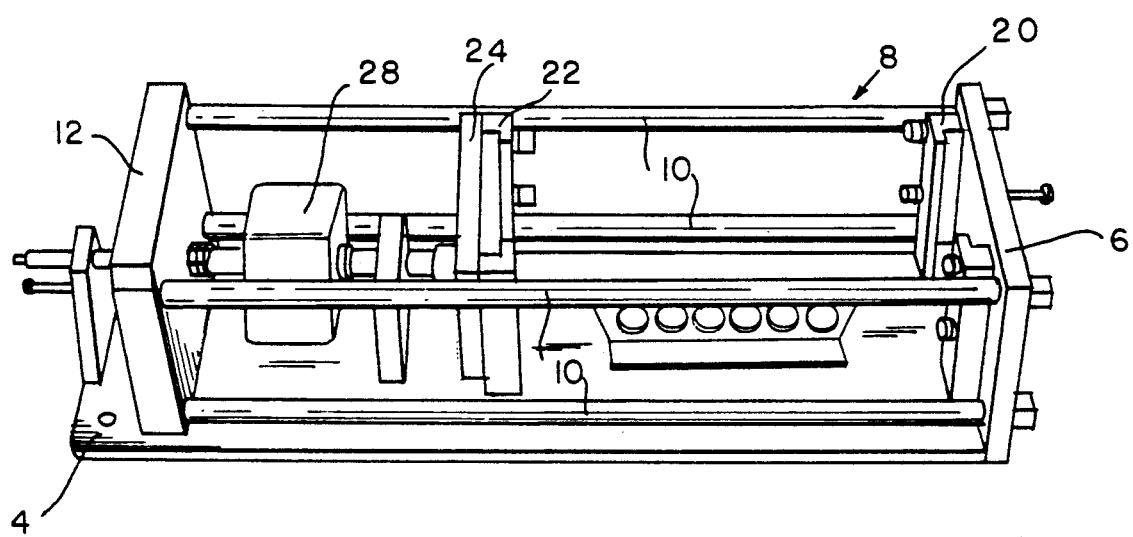
FIG. 2 is a perspective view of the device of FIG. 1 with the sample removed.
Figure 3:
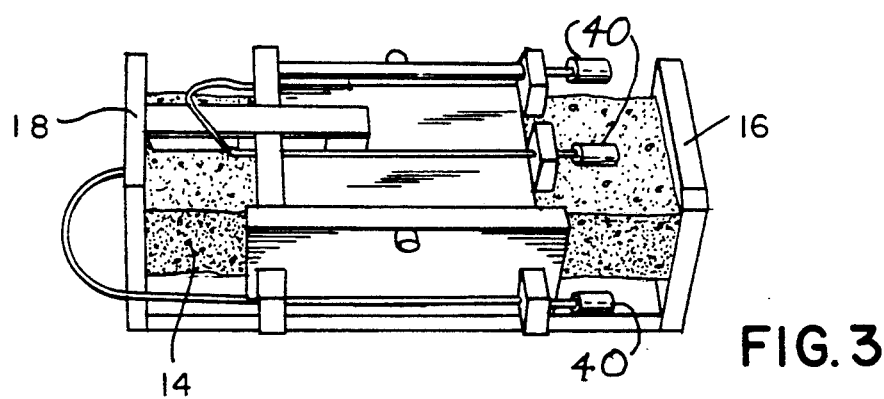
FIG. 3 is a perspective view of the sample and a jig for alignment and mounting of the linear variable differential transformers.

Referring to FIGS. 1-3, the portable device for measuring thermal stresses and strains in an asphalt sample will now be described. The device includes a fixture 2 including a base 4, a first fixed end wall 6, and a cage assembly 8. The cage assembly includes four spaced parallel rods 10 having a low coefficient of thermal expansion connected at one end with the fixed end wall 6 and a second end wall 12 with which the free ends of the rods are connected.

As shown in FIG. 1, a sample 14 of asphalt pavement is suspended within the fixture. The sample is approximately twelve inches in length and up to three inches square. This is significantly larger than those samples accommodated by the prior devices enabling more accurate measurements of mechanical properties to be made. The sample is suspended between a pair of mounting plates 16, 18 which preferably are pre-assembled and epoxied to the ends of the sample as shown in FIG. 3. The first mounting plate 16 is installed in retaining members 20 of the fixed end wall 6 of the fixture and the second mounting plate 18 is installed in retaining members 22 of a floating plate 24 connected with the second end wall 12 via a first rod 26, a load cell 28, and a second rod 30. The first rod 26 is slidably supported by a fixed support 32 attached to base 4 and passes through an opening in the second end wall 12 for connecting with the load cell 28. The second rod 30 is slidably supported by a fixed support 34 attached to base 4 and is connected at its end with the load cell 28 and the floating plate 24. The floating plate 24 may thus float or slide between the rods 10.

Once the sample is arranged in the fixture, it is preloaded using two preload nuts 36 (only one of which is shown) on either side of the second end wall 12 of the cage assembly threadably connected with the first rod 26. The preload nuts are locked in position with locking nuts 38.

As shown in FIGS. 1 and 3, linear variable differential transformers 40 are mounted on the sample. As will be developed below, the transformers produce an output signal to a data acquisition system 42 representing thermal strains in the sample.

The load cell 28 is connected between the second end wall 12 and the floating plate 24 via the rods 26 and 30. The load cell detects forces between the sample and the end wall resulting from thermal stresses in the sample. The cell produces an output signal to the data acquisition system 42 corresponding to the axial thermal stress in the sample. A first temperature sensor 44 monitors the temperature of the sample. A second temperature sensor 46 monitors the ambient temperature. The temperature sensors may comprise thermocouples. The sensed temperatures are delivered to the data acquisition system.

With the sample mounted in the fixture, the entire fixture is arranged in an enclosed chamber (not shown) which includes a source of heated or cooled air. The air is directed around the sample to induce thermal strains and stresses therein which are detected by the linear variable differential transformer and the load cell, respectively. Temperatures of the sample and air are detected by the temperatures sensors. The stress, strain and temperatures signals are processed and stored in the data acquisition system. Based upon the thermal stress and strain results, the proper asphalt composition for a particular environment can be formulated.

The present invention is a significant improvement over the prior art in that it affords greater flexibility in sample size, heat transfer occurs through air rather than a liquid medium, and strains on the sample may be measured as well as stress. The fixture is compact and portable enabling the user to perform on-site testing to accurately simulate field conditions with respect to environment. Finally, the four-rod cage assembly minimizes fixture induced stresses and strains due to the low coefficient of expansion rods and the equal distribution of forces accomplished by the cage configuration.

Alternate constructions of the fixture may be used without deviating from the inventive concepts thereof. For example, a large, C-shaped air-cooled device may be used for larger samples. Moreover, a plurality of fixtures may be ganged to simultaneously test a number of samples.

What is claimed is:

1. Apparatus for measuring thermal stresses and strains in asphalt pavement samples, comprising
   (a) a fixture including a base;
   (b) means connected with said base for mounting the sample thereon; and
   (c) means for directing an air flow of variable temperature onto the sample; and
   (d) means for sensing thermal stresses and strains and temperature fluctuations induced in the sample in response to the air flow; and
   (e) wherein said sensing means comprises
      (1) at least one linear variable differential transformer mounted on the sample for producing a displacement output signal in response to thermal strains therein;
      (2) a load cell connected with said mounting means for producing a force output signal in response to thermal stresses in the sample; and
      (3) temperature sensing means for producing temperature output signals corresponding to sample temperature and ambient temperature; and
   (f) wherein the fixture further includes a thermally stable cage having a fixed end wall and a floating plate, said mounting means including a first mounting plate connected with the fixed end wall of said cage and a second mounting plate connected with said floating plate for sliding movement, said load cell being connected at one end with said floating plate for detecting force transmitted through said second mounting plate in response to the thermal stress.

2. Apparatus as defined claim 1, wherein said cage further comprises a second end wall and a plurality of spaced parallel rods having opposite ends connected with said first and second end walls, said load cell being connected at its other end with said second end wall of said cage, whereby said load cell responds to forces on said floating plate with respect to said end walls.

3. Apparatus as defined in claim 2, and further comprising a data acquisition system connected with said linear variable differential transformer, said load cell, and said temperature sensing means for receiving and storing said displacement, force, and temperature output signals.

* * * * *